US010000660B2

(12) United States Patent
Van Gaalen et al.

(10) Patent No.: US 10,000,660 B2
(45) Date of Patent: Jun. 19, 2018

(54) THIOL-FUNCTIONAL COMPOUND

(71) Applicant: AKZO NOBEL COATINGS INTERNATIONAL B.V., Arnhem (NL)

(72) Inventors: Ronald Petrus Clemens Van Gaalen, Leiden (NL); Rogier Van Gemert, Leiden (NL); Hendrik Jan Willem Van Den Haak, Sassenheim (NL); Nicolaas Jacob Van Beelen, Katwijk aan Zee (NL)

(73) Assignee: AKZO NOBEL COATINGS INTERNATIONAL B.V., Arnhem (NL)

( * ) Notice: Subject to any disclaimer, the term of this patent is extended or adjusted under 35 U.S.C. 154(b) by 0 days. days.

(21) Appl. No.: 14/649,618

(22) PCT Filed: Dec. 9, 2013

(86) PCT No.: PCT/EP2013/075889
§ 371 (c)(1),
(2) Date: Jun. 4, 2015

(87) PCT Pub. No.: WO2014/090716
PCT Pub. Date: Jun. 19, 2014

(65) Prior Publication Data
US 2015/0315415 A1 Nov. 5, 2015

Related U.S. Application Data

(60) Provisional application No. 61/736,224, filed on Dec. 12, 2012.

(30) Foreign Application Priority Data

Dec. 11, 2012 (EP) ..................................... 12196564

(51) Int. Cl.
C09D 175/06 (2006.01)
C07C 319/18 (2006.01)
C07C 323/52 (2006.01)
C08G 18/38 (2006.01)
C08G 18/62 (2006.01)
C09D 175/04 (2006.01)
C08G 18/79 (2006.01)
C08G 18/46 (2006.01)

(52) U.S. Cl.
CPC .......... *C09D 175/06* (2013.01); *C07C 319/18* (2013.01); *C07C 323/52* (2013.01); *C08G 18/38* (2013.01); *C08G 18/3876* (2013.01); *C08G 18/4676* (2013.01); *C08G 18/62* (2013.01); *C08G 18/792* (2013.01); *C09D 175/04* (2013.01)

(58) Field of Classification Search
CPC ..... C07C 319/18; C07C 323/52; C08G 18/38; C08G 18/3876; C08G 18/4676; C08G 18/62; C08G 18/792

USPC ........................................................ 560/154
See application file for complete search history.

(56) References Cited

U.S. PATENT DOCUMENTS

| 3,853,728 | A | * | 12/1974 | Wrzesinski | ............... | C09G 1/10 |
| | | | | | | 106/10 |
| 4,199,495 | A | | 4/1980 | Minagawa et al. | | |
| 4,305,867 | A | | 12/1981 | Michaelis et al. | | |
| 4,882,449 | A | * | 11/1989 | Harris | ...................... | C07C 59/70 |
| | | | | | | 556/419 |
| 5,128,424 | A | | 7/1992 | McGinnis et al. | | |
| 5,352,757 | A | * | 10/1994 | Lavault | .................. | C07C 323/52 |
| | | | | | | 528/376 |
| 7,318,966 | B2 | * | 1/2008 | Tominaga | ............... | C07C 15/28 |
| | | | | | | 257/40 |
| 2008/0132601 | A1 | * | 6/2008 | Hoyle | ....................... | C08F 2/50 |
| | | | | | | 522/180 |
| 2008/0206153 | A1 | | 8/2008 | Winter et al. | | |
| 2009/0047443 | A1 | * | 2/2009 | Bowman | ................ | B05D 7/536 |
| | | | | | | 427/553 |
| 2010/0047713 | A1 | * | 2/2010 | Murofushi | ............ | G03F 7/0275 |
| | | | | | | 430/281.1 |

(Continued)

FOREIGN PATENT DOCUMENTS

DE 10 2005 003 01 7/2006
EP 0 213 701 3/1987

(Continued)

OTHER PUBLICATIONS

Ksenia Pumpor et al., Hexafluoroacetone as a Protecting and Activating Reagent. Regioselective Esterification of Aspartic, Malic, and Thiomalic Acid, Monatashefte fur Chemie—Chemical Monthly, vol. 135, issue 11, pp. 1427-1443, (2014).
Harry Adams et al: "Selective adsorption in gold-thiol monolayers of calix-4-resorcinarenes", Journal of the Chemical Society, Chemical Communications, No. 21, Jan. 1, 1994 (Jan. 1, 2004), pp. 2527-2529, GB ISSN: 0022-4936, DOI: 10.1 039/C39940002527.
Jeremy M. Beebe et al: "Length Dependence of Charge Transport in Nanoscopic Molecular Junctions Incorporating a Series of Rigid ThiolTerminated Norbornylogs", Journal of Physical Chemistry Part B: Condensed Matter, Materials, Surfaces, Interfaces & Biophysical, vol. 109, No. 11, Mar. 1, 2005 (Mar. 1, 2005), pp. 5207-5215, US ISSN: 1520-6106, DOI: 10.1021/jp044630p.

(Continued)

*Primary Examiner* — Kelechi Egwim
(74) *Attorney, Agent, or Firm* — McDonnell Boehnen Hulbert & Berghoff LLP

(57) ABSTRACT

The invention relates to a thiol-functional organic compound having on average at least 3.1 thiol groups per molecule, and having carbon atoms, oxygen atoms, and sulfur atoms, and optionally further heteroatoms, and wherein the ratio of the number of carbon atoms (C) to the sum of the number of heteroatoms (HA), (C/HA) is at least 2.0, and wherein the thiol groups are derived from 2-mercapto acetic acid, 2-mercapto propionic acid, or 3-mercapto propionic acid, or esters thereof; and to a liquid coating composition comprising the thiol-functional compound and a thiol-reactive crosslinker.

13 Claims, No Drawings

(56) References Cited

U.S. PATENT DOCUMENTS

2010/0087611 A1    4/2010    Urakawa et al.

FOREIGN PATENT DOCUMENTS

| EP | 0 448 224 | 9/1991 |
|---|---|---|
| EP | 2 030 989 | 3/2009 |
| WO | WO 01/92362 | 12/2001 |
| WO | WO 01/92363 | 12/2001 |
| WO | WO 2006/064035 | 6/2006 |
| WO | WO 2008/082176 | 7/2008 |

OTHER PUBLICATIONS

Xun Yan et al: "A Polymenzed Calix[b]arene Monolayer Having Gas Permeation Selectivity that Exceeds Knudsen Diffusion", Journal of the American Chemical Society, vol. 124, No. 37, Sep. 1, 2002 (Sep. 1, 2002), pp. 10962-10963, US ISSN: 0002-7863,DOI: 10.1021/ja0274305.

Eric Busseron et al: "Guest Recognition in a Partially Bridged Deep Cavitand", Organic Letters, 14(23),6012-6015 CODEN: ORLEF7; ISSN: 1523-7052, vol. 12, No. 21, Nov. 5, 2010 (Nov. 5, 2010), pp. 4828-4831, ISSN: 1523-7060, 001: 10.1021101101980f.

Nadim Darwish et al: "Observation of Electrochemically Controlled Quantum Interference in a Single Anthraquinone-Based Norbornylogous Bridge olecule", Angewandte Chemie International Edition, vol. 51, No. 13, Mar. 26, 2012 (Mar. 26, 2012), pp. 3203-3206, ISSN: 1433-7851, DOI: 10.1 002/anie.2011 07765.

Niece Krista L et al: "Self-assembly combining two bioactive peptide-amphiphile molecules into nanotibers by electrostatic attraction", Journal of the American Chemical Society, American Chemical Society, US, vol. 125, No. 24, Jun. 18, 2003 (Jun. 18, 2003), pp. 7146-7147, ISSN: 0002-7863,DOI: 10.1021/JA028215R.

Zhong W et al: "Development of highly pure @a-helical lipoglycopeptides as self-adjuvanting vaccines", Tetrahedron, Elsevier Science Publishers, Amsterdam, NL, vol. 65, No. 17, Apr. 25, 2009 (Apr. 25, 2004), pp. 3459-3464, ISSN: 0040-4020, DOI: 10.1 016/J.TET.2009.02.060.

Moyle et al: "A technique for the synthesis of highly-pure, monoepitopic, multi-valent lipid core peptide vaccines", Tetrahedron Letters, Elsevier, Amsterdam, NL, vol. 48, No. 29, Jul. 16, 2007 (Jul. 16, 2007), pp. 4965-4967, ISSN: 0040-4039, DOI: 10.1 016/J.TETLET.2007.05.129.

* cited by examiner

THIOL-FUNCTIONAL COMPOUND

REFERENCE TO RELATED APPLICATIONS

This application is the U.S. National Phase of PCT/EP2013/075889, filed on Dec. 9, 2013, and claims the benefit of EP Application No. 12196564.4, filed on Dec. 11, 2012, and U.S. Provisional Application No. 61/736,224, filed on Dec. 12, 2012.

The invention relates to a thiol-functional compound having more than 3 thiol groups per molecule, and to a coating composition comprising the thiol-functional compound.

The use of thiol-functional compounds in coating compositions is known, for example from International patent application WO 01/92362. Frequently used thiol-functional compounds are esters of mercapto carboxylic acids and polyols, for example the esters of 3-mercapto propionic acid and pentaerythritol, dipentaerythritol or trimethylol propane. Thiol-functional compounds with an average thiol functionality of 3 or lower have been found to lead to insufficient crosslinking and long drying times. A drawback of the known compounds of sufficient thiol functionality is their limited compatibility with other components of paint systems, in particular binders and crosslinkers. This limits the amount of thiol-functional compounds which can be included in coating compositions as reactive diluents without causing adverse effects. It also sets limits on the types of binders with which these thiol-functional compounds can be combined. For example, these compounds can only be combined with most OH-functional polyacrylates in very limited amounts, as these combinations often do not result in clear coating films.

German patent application DE 102005003010 A describes copolymers for cosmetic applications. The copolymers are prepared in the presence of polyfunctional chain transfer agents. Among many others, this document also describes pentaerythritol tetrakis 5-mercaptopentanoate and pentaerythritol tetrakis 6-mercaptohexanoate as chain transfer agents. A drawback of these tetra-functional thiols is that the thiol groups are derived from mercapto-carboxylic acids which are not readily available on industrial scale. Use of such mercapto carboxylic acids would bring about unacceptable costs for coating applications.

The invention seeks to provide thiol-functional compounds which are not limited by the above-mentioned drawbacks.

The invention now provides organic thiol-functional compounds having at least 3.1 thiol groups per molecule, and having carbon atoms, oxygen atoms, and sulfur atoms, and optionally further heteroatoms, and wherein the ratio of the number of carbon atoms (C) to the sum of the number of heteroatoms (HA), (C/HA) is at least 2.0, and wherein the thiol groups are derived from 2-mercapto acetic acid, 2-mercapto propionic acid, or 3-mercapto propionic acid, or esters thereof.

It has been found that thiol-functional compounds according to the invention have an improved compatibility with other components of paint systems. As a consequence, increased amounts of such thiol-functional compounds can be included in coating compositions as reactive diluents without causing adverse effects. The thiol-functional compounds of the invention can also be combined with OH-functional acrylic polymers without causing compatibility problems. The thiol groups are derived from mercapto-carboxylic acids which are readily available on industrial scale and at acceptable costs.

In the context of the atom number ratio, the expression heteroatoms includes all elements, except carbon and hydrogen. In some embodiments, the thiol-functional compounds contain only oxygen and sulfur as heteroatoms. However, it is also possible that the thiol-functional compounds contain further heteroatoms, such as nitrogen, halogens, or phosphorus.

As mentioned above, the ratio of the number of carbon atoms (C) to the sum of the number of heteroatoms (HA), (C/HA) is at least 2.0. In a preferred embodiment, this ratio is at least 2.1. Generally, the ratio does not exceed 4.0. The atom ratios described above can be calculated from the chemical structures of the compounds, if these are known. Alternatively, it is also possible to determine these ratios by analytical methods, for example combustion analysis.

Suitable thiol-functional compounds have more than 3.0 thiol groups per molecule. Typically, the compounds have 3.1 to 6.0 thiol groups per molecule. Preferably, the compounds have at least 3.4 thiol groups, or at least 3.6 thiol groups per molecule. Generally, the compounds do not have more than 7.0 thiol groups per molecule.

It is to be understood that the thiol-functional compounds of the invention often are present as a mixture of different compounds, wherein the number of thiol groups of individual compounds may vary. Therefore, the number of thiol groups per molecule as used herein refers to the average number of thiol groups of the molecules present in the mixture. The average number of thiol groups refers to the number average, i.e. the total number of thiol groups divided by the number of molecules. In many cases the average functionality can be calculated as theoretical thiol functionality based on the known functionalities of starting materials and their molar ratios. When polymeric compounds are involved, their theoretical number average molecular weight may be used as a basis for the calculation. Alternatively, number average molecular weights determined by gel permeation chromatography can be used. In a preferred embodiment, the thiol-functional compounds are liquids at room temperature, for example at 23° C. Generally, the thiol-functional compounds have a viscosity at 23° C. in the range of 2 to 100 Pa·s. In a preferred embodiment, the thiol-functional compounds have a low viscosity, for example in the range of 10 to 35 Pa·s at 23° C. Low viscosity thiol-functional compounds have the additional advantage that their use in coating compositions reduces the amount of volatile organic solvents required to achieve the desired application viscosity.

The viscosity mentioned above refers to a viscosity measured using a Brookfield CAP2000+ viscometer. Cone type and speed were selected in such a way that the measured value was between 20 and 80% of the maximum reading specified by the manufacturer.

The thiol-functional compounds of the invention generally are non-volatile compounds, which means that their boiling point at atmospheric pressure exceeds 250° C. The molecular weight of the thiol-functional compounds typically is at least 500, preferably at least 600, or even 700 or 800. The molecular weight generally does not exceed 10.000, and preferably is at most 5,000, or 2,500. Where mixtures having a molecular weight distribution are concerned, the aforementioned molecular weights refer to the number average molecular weight determined by gel permeation chromatography, using polystyrene as standard.

In one embodiment, the thiol-functional compound according to the invention can be obtained by modification of a thiol-functional precursor compound. To this end, a thiol-functional precursor compound wherein the ratio of the number of carbon atoms to the sum of the number of heteroatoms (C/(HA)) is below 2.0 may be reacted with a carbon rich compound, resulting in a thiol-functional compound wherein the (C/(HA)) is 2.0 or higher. Examples of such a reaction are the reaction of a part of the thiol groups of a thiol-functional precursor compound with an epoxide-functional compound or with an acryloyl-functional compound.

The thiol-functional precursor compound is typically an ester of a polyol with a mercapto carboxylic acid used in the invention. Such esters are generally known and commercially available. Examples of polyols include pentaerythritol, di-trimethylolpropane, and di-pentaerythritol. Mercapto carboxylic acids are 2-mercapto acetic acid, and 2- and 3-mercapto propionic acid. Typically, the polyols are essentially fully esterified with the mercapto carboxylic acids mentioned above. However, lower degrees of esterification or esterification with other carboxylic acids is possible as well, provided that the final thiol-functional compound meets the requirements in terms of thiol functionality.

In one embodiment, a part of the thiol groups of the thiol-functional precursor compounds is reacted with a thiol-reactive compound. Examples of suitable thiol-reactive compounds are isocyanate-functional compounds, olefinically unsaturated compounds, and epoxide-functional compounds. Suitable epoxide compounds are glycidyl ethers and glycidyl esters, as well as epoxides obtainable by epoxidation of olefinically unsaturated compounds, for example derivatives of epoxidized fatty acids. When monofunctional epoxides are used, the thiol functionality of the reaction product is reduced relative to the thiol-functional precursor compound, proportional to the molar ratio of thiol groups and epoxide groups reacted. Examples of suitable monofunctional epoxides are the glycidyl esters of carboxylic acids and glycidyl ethers of alcohols. Preferably, the carboxylic acids or alcohols have at least 8 carbon atoms. The carboxylic acids or alcohols may be linear or branched. The glycidyl ester of versatic acid, commercially available under the trade designation Cardura E10, has been found to be particularly suitable.

However, it is also possible to use di- or higher-functional epoxides. In this case, two or more thiol-functional precursor compound molecules are linked together when a part of the thiol groups is reacted with the epoxide groups. This route is particularly attractive when higher-functional thiol compounds are required, or when the thiol-functional precursor compounds have a low thiol functionality. Examples of suitable difunctional epoxides are glycidyl ethers of, optionally hydrogenated, bisphenol A, and epoxidized vegetable oils.

In one embodiment, the thiol-functional compound additionally comprises one or more hydroxyl groups. The hydroxyl groups may be derived from the reaction of thiol groups and epoxide groups, as described above.

It should be noted that the reaction of dithiols with epoxide compounds is known, for example from International patent application WO 2008/082176. This document is concerned with cationic electrodeposition resin compositions.

The thiol-functional compounds of the invention can alternatively be obtained by a process wherein polyols are esterified with a mixture of one or more mercapto carboxylic acids as mentioned above, and a further carboxylic acid or ester-forming derivative thereof. Preferably, the further carboxylic acid has at least 8 carbon atoms. The further carboxylic acid may also have more than one carboxylic acid groups. Dimer fatty acids may be specifically mentioned. Dimer fatty acids are commercially available under the trade designation Pripol ex Croda. In a further embodiment it is preferred that the further carboxylic acid is branched. As specific example the reaction product of 1 mole of di-pentaerythritol, 4 moles of 3-mercapto propionic acid, and 2 moles of isononanoic acid may be mentioned.

In some preferred embodiments, the thiol-functional compounds of the invention have a low surface tension, for example a surface tension not exceeding 50 dyne/cm. Typically, the surface tension is in the range of 35 to 45 mN/m, whereas the esters of 3-mercapto propionic acid and pentaerythritol or dipentaerythritol have total surface tensions of 51.3 and 51.2 mN/m, respectively. Surface tensions can be measured with the Du Nouy ring method or calculated from additive atomic increments starting from the nominal chemical structure with the computer program ACD/Chemsketch.

It should be noted that the thiol-functional compounds prepared by the methods described above generally comprise mixtures of compounds. Therefore, it is to be understood that the properties and features described relate to average values of mixtures of compounds, or polymers or oligomers having a molecular weight distribution. Alternatively, when the reaction products are pure or purified compounds, the values and features refer to these specific compounds.

The invention also relates to a liquid coating composition comprising the thiol-functional compound described above, and a thiol-reactive crosslinker.

The liquid coating composition typically is a non-aqueous coating composition comprising a volatile organic solvent and having a high non-volatile content. The thiol-reactive crosslinker may have a plurality of functional groups selected from epoxide, olefinically unsaturated groups, such as acrylic unsaturation, isocyanate, or mixtures thereof. The coating compositions may be putties or fillers, primers with rapid drying properties, as well as top coats or clear coats. The thiol-functional compounds can also be used with great advantage in UV-curable compositions. Preferably, the coating composition comprises, next to the thiol-functional compound, additional binders or film-forming resins, such as hydroxyl-functional polyacrylates or hydroxyl-functional polyesters.

Specific coating compositions wherein the thiol-functional compounds of the invention can be used are described in International patent application WO 01/92362, which is incorporated by reference.

EXAMPLES

Raw Materials Used

ACE (reaction product of acrylic acid and Cardura E10) and Cardura E10 were obtained from Momentive.
Trimethylolpropane trimethacrylate was obtained from Aldrich.
Perkadox AMBN was obtained from AkzoNobel.
CGI277 is a photobase from BASF.
Dipentaerythritol, with the quality name di-penta 93, was obtained from Perstorp polyols.
Pentaerythritol was obtained from Perstorp polyols.
Setalux 1753, 1157, 1160: acrylic polyol resins solutions ex Nuplex Resins
Setalux 2120: thermoplastic acrylic resin ex Nuplex Resins
Vikoflex: epoxidized soybean oil ex Arkema
CAB381, CAB551: cellulose acetate/butyrate ex Eastman
Laropal A81: aldehyde resin ex BASF Pentaerythritol tetra 3-mercaptopropionate (PTMP) and dipentaerythritol hexa 3-mercaptopropionate ex Bruno Bock
Tolonate HDT-LV: polyisocyanate ex Perstorp
Vestanat T1890: polyisocyanate ex Evonik
DOT: dioctyltin dilaurate
Pripol 1009: Dimer fatty acid ex Croda Example 1

Preparation of a Thiol-Functional Compound 1 mole of di-pentaerythritol hexa(3-mercapto propionate) and 2 moles of versatic acid glycidyl ester (Cardura E10) were charged into a 2,000 ml four-necked round-bottomed flask equipped with mechanical stirrer, heating mantle, thermocouple, reflux cooler, and nitrogen inlet. The batch was made inert by breaking a vacuum 3 times with a nitrogen flow. The reaction mixture was heated to 150° C. and kept at this temperature until the epoxy value was 8 mg KOH/g, determined according to ISO 3001. The reaction time was about 10 hours. Thereafter, the reaction mixture was cooled to room temperature. GPC (PLmix column) showed an Mn of 1,184 and an Mw of 1,887. A viscosity of 17 Pa·s were measured using cone number 6 @ 100 rpm. A total surface tension of 33.5 mN/m was measured.

The material has a theoretical molecular formula $C_{54}H_{94}O_{19}S_6$ and C/HA=2.16 and a theoretical average SH-functionality of 4.0.

Example 2

Compatibility Tests

The improved compatibility of the compound according to the invention was shown by preparing mixtures of commercial binders with either pentaerythritol tetra(3-mercaptopropionate) or the material from Example 1, and judging the compatibility of the mixtures visually. Table 1 summarizes the results obtained when binders were mixed in a 1:1 weight ratio with the thiol-functional compounds. Table 2 summarizes results wherein binders were mixed with the thiol-functional compound in a 2:1 weight ratio.
Compatibility:
+=completely miscible,
+/−=borderline,
−=immiscible.

TABLE 1

| Binder | PTMP<br>C/HA = 1.42 | Example 1<br>C/HA = 2.16 |
|---|---|---|
| Setalux 1753 | +/− | + |
| Setalux 1160 | − | + |
| Vikoflex | − | + |

TABLE 2

| Binder | PTMP<br>C/HA = 1.42 | Example 1<br>C/HA = 2.16 |
|---|---|---|
| CAB 381 | +/− | + |
| CAB 551 | − | + |
| Seta lux 2120 | − | +/− |
| Laropal A81 | +/− | + |

It can be inferred from Tables 1 and 2 that the thiol-functional compound of Example 1 according to the invention has a better compatibility and miscibility with commercial binders of variable structure than the known thiol-functional compound PTMP.

Example 3

Preparation of a Thiol-Functional Compound

Into a 2-liter four-necked round-bottomed flask equipped with mechanical stirrer, thermocouple, distillation equipment, and nitrogen inlet the following materials were charged: dipentaerythritol (343.97 grams), isononanoic acid (427.89 grams), and 3-mercaptopropionic acid (574.07 grams). The batch was made inert by breaking a vacuum 3 times with a nitrogen flow. Then methanesulfonic acid (1.06 grams) was added. The batch was slowly heated to 150° C. The distillation of reaction water started at 133° C. The mixture was kept at 150° C. and a reduced pressure of about 200 mbar was applied. Two further portions of 1.06 grams of methanesulfonic acid were added during the reaction. The reaction was continued until an acid value of 10 mg KOH/gram was obtained (about 20 hours). GPC (Oligopore column) showed an Mn of 917 and an Mw of 1,037.

The material has a theoretical molecular formula $C_{40}H_{70}O_{13}S_4$ and C/HA=2.35 and a theoretical average SH-functionality of 4.0. A viscosity of 2.4 Pa·s was measured using cone #3 @ 200 rpm.

Example 4

Preparation of a Thiol-Functional Compound

Into a 1-liter four-necked round-bottomed flask equipped with mechanical stirrer, thermocouple, distillation equipment, and nitrogen inlet the following materials were charged: dipentaerythritol (138.35 grams), 12-hydroxystearic acid (326.9 grams), and 3-mercaptopropionic acid (230.89 grams). The batch was made inert by breaking a vacuum 3 times with a nitrogen flow. Then methanesulfonic acid (0.43 gram) was added. The batch was slowly heated to 150° C. The distillation of reaction water started at 123° C. The mixture was kept at 150° C. and a reduced pressure of about 200 mbar was applied. The reaction was continued until an acid value of 5 mg KOH/gram was obtained (about 12 hours). GPC (Mixed C column) showed an Mn of 1,646 and an Mw of 2,973.

The material has a theoretical molecular formula $C_{50}H_{106}O_{15}S_4$ and C/HA=2.63 and a theoretical average SH-functionality of 4.0. A viscosity of 5.1 Pa·s was measured using cone #3 @ 200 rpm.

Example 5

Preparation of a Thiol-Functional Compound 266.07 grams of pentaerythritol tetrakis 3-mercaptopropionate (PTMP) were pre-charged into a 1-liter four-necked round-bottomed flask equipped with mechanical stirrer, thermo couple, reflux condenser, and nitrogen inlet. The batch was made inert by breaking a vacuum 3 times with a nitrogen flow and is slowly heated to 80° C. Then a mixture of ACE (acrylic acid—Cardura E10) (172.53 grams), trimethylolpropane trimethacrylate (61.37 grams), and 1,000 ppm of Perkadox AMBN was dosed in 2.5 hours to the round-bottomed flask at a temperature of 80° C. The batch was stirred for 2 hours more at this temperature as a post-reaction. NMR showed that the acrylic double bonds had fully reacted. GPC (Polypore column) showed an Mn of 1,499 and an Mw of 3,927. A viscosity of 56 Pa·s was measured using cone #6 @ 50 rpm.

A total surface tension of 36.2 mN/m was measured. The material has an Mn of 1,385, an Mw of 3,632, a theoretical molecular formula $C_{120}H_{198}O_{47}S_{12}$ and C/HA=2.03, and a theoretical average SH-functionality of 6.0.

Example 6

Preparation of Clear Coating Compositions According to the Invention and Comparative Compositions For each composition the A, B, and C components were prepared individually by mixing the ingredients indicated in Table 3 below. Before application the A, B, and C components were mixed together, adjusted to a viscosity of 16 seconds DIN cup 4 with butyl acetate, and applied on door panels over a basecoat (Autowave MM VWLY9Z ex AkzoNobel), using a SATA RP 4000 1.3 spray gun. Clear coats were applied in two layers, with a flash-off of 2 minutes between layers. On one side of the panel an additional layer was sprayed, in order to judge sagging. After another 2 minutes of flash-off UV exposure was carried out with a Panacol handheld Lamp 400 W. This was done two to three times as if spraying at a distance of 20-30 cm from the panel. During application, sprayability, wetting, flow, and sagging on vertical parts were evaluated. After these evaluations EHO (Enamel Hold Out), clearness, gloss, craters, and pinholes were evaluated. This was done on the same day and the next. The touch dry time was evaluated immediately after UV-exposure.

In Comparative Examples 6ac and 6bc a thiol-functional polyester was used in combination with PTMP. Clear films were obtained, but the sprayability, wetting, flow, and sagging were at best borderline. However, when the PTMP was replaced with the compound of Example 1, clear films with good application properties were obtained (Example 6ci).

When the thiol-functional polyester in Comparative Examples 6ac and 6bc was replaced with an OH-functional acrylic (Comparative Examples 6dc and 6fc), the application properties were good, but no clear films were obtained. However, when in these formulations PTMP was replaced with the thiol-functional compounds of Examples 1, 3, 4, and 5, respectively, (Examples 6ei, 6gi, 6hi, 6ii, and 6ji) compositions were obtained which both gave clear films and had excellent application properties.

In Comparative Example 6kc an acrylic was combined with the SH-functional polyester. Clear films were obtained, but due to the high viscosity of the polyester the VOC level at spraying viscosity was high. Moreover, due to the relatively low SH-functionality of the polyester the touch dry time was long.

TABLE 3

| Example 6 | ac | bc | ci | dc | ei | fc | gi | hi | ii | ji | kc |
|---|---|---|---|---|---|---|---|---|---|---|---|
| A Component | | | | | | | | | | | |
| Thiol polyester | 56.9 | 28.4 | 28.4 | | | | | | | | 86.5 |
| Setalux 1157 XS54 | | | | 58.3 | 58.3 | | | | | | |
| Setalux 1753 XS70 | | | | | | 48.1 | 48.1 | 48.1 | 48.1 | 48.1 | 48.1 |
| PTMP | 24.6 | 32.8 | | 32.8 | | 32.8 | | | | | |
| Example 1 | | | 55.0 | | 55.0 | | 50.1 | | | | |
| Example 3 | | | | | | | | 54.2 | | | |
| Example 4 | | | | | | | | | 55.5 | | |
| Example 5 | | | | | | | | | | 65.5 | |
| Byk 306 | 1.1 | 1.1 | 1.1 | 1.1 | 1.1 | 1.7 | 1.7 | 1.7 | 1.7 | 1.7 | 1.9 |
| Byk 355 | | | | | | | | | | | |
| Tinuvin 400 | 2.0 | 2.0 | 2.2 | 2.0 | 2.3 | 2.2 | 2.2 | 2.3 | 2.0 | 2.4 | 2.4 |
| Tinuvin 123 | 0.8 | 0.7 | 0.8 | 0.7 | 0.8 | 0.8 | 0.8 | 0.8 | 0.8 | 0.8 | 0.9 |
| 11.8% DOT in butyl acetate | 3.3 | 3.3 | 3.3 | 3.3 | 3.3 | 3.3 | 4.2 | 4.3 | 3.9 | 4.6 | 4.6 |
| B Component | | | | | | | | | | | |
| Butyl Acetate | 50.0 | 50.0 | 50.0 | 50.0 | 50.0 | 41.4 | 41.4 | 41.4 | 41.4 | 41.4 | 41.4 |
| Tolonate HDT LV | 100.0 | 100.0 | 100.0 | 100.0 | 100.0 | 77.6 | 77.6 | 77.6 | 77.6 | 77.6 | 77.6 |
| Vestanat T1890E | | | | | | 12.0 | 12.0 | 12.0 | 12.0 | 12.0 | 12.0 |
| C Component | | | | | | | | | | | |
| Xylene | 9.0 | 9.0 | 9.9 | 9.9 | 9.9 | 9.9 | 9.9 | 9.9 | 9.9 | 9.9 | 10.9 |
| CGI277 | 1.0 | 1.0 | 1.1 | 1.1 | 1.1 | 1.1 | 1.1 | 1.1 | 1.1 | 1.1 | 1.2 |
| Butyl acetate | 13.2 | 13.2 | 23.3 | 23.3 | 29.3 | 43.3 | 48.3 | 38.3 | 38.3 | 23.3 | 53.2 |
| VOC@16 s DC4 (gram/liter) | 320 | 320 | 410 | 340 | 410 | 420 | 420 | 390 | 380 | 370 | 460 |
| Application/Coating Results | | | | | | | | | | | |
| Clearness | ++ | ++ | ++ | -- | ++ | - | ++ | ++ | ++ | ++ | ++ |
| Sprayability/Wetting | +/- | - | + | + | ++ | + | ++ | ++ | ++ | ++ | n.d. |
| Flow/Sagging | - | -- | + | + | ++ | + | ++ | ++ | ++ | ++ | n.d. |
| Touch dry time (minutes) | 10 | 5 | 10 | 5 | 10 | 5 | 10 | 10 | 10 | 10 | 45 |

Comparative Thiol-Functional Polyester

The thiol-functional polyester used in Examples 6ac, bc, ci and kc was prepared in a two-step process.

In the first step a polyester polyol was prepared from the following components:

| | |
|---|---|
| Hexahydrophthalic anhydride | 203.76 g |
| Trimethylol propane | 264.60 g |
| Isononanic acid | 97.35 g |
| Dimethylolcyclohexane | 5.21 g |
| Adipic acid | 5.77 g |
| Aqueous solution of 85% phosphoric acid | 0.49 g |

The components were placed in a 2-liter glass 4-necked reactor equipped with stirrer, packed column, condenser, heating mantle, thermocouple, temperature controls, vacuum line, and nitrogen inlet. The reaction mixture was heated under a nitrogen stream. The temperature of the mixture was gradually raised to 240° C. The reaction water was distilled off at such a rate that the temperature at the top of the packed column did not exceed 103° C. Finally, vacuum of 200 mbar was applied while maintaining the nitrogen stream, and the reaction was run at 240° C. for one hour until an acid value below 5 mg KOH/g is reached. The mixture was cooled to about 100° C.

In the second step the hydroxyl-functional polyester polyol was esterified with 3-mercaptopropionic acid to form thiol-functional polyester. 211 g 3-mercaptopropionic acid were added at atmospheric pressure. The esterification reaction was carried out at 150° C. for 2-3 hours under vacuum (maintaining the nitrogen flow) until an acid value of approx. 80 mg KOH/g was reached. Then 0.26 g of methane sulfonic acid was added and the esterification was continued to an acid value between 25-30 mg KOH/g. Another portion of 0.26 g of methane sulfonic acid was added and the esterification was continued until an acid value of <10 mg KOH/g was reached. High vacuum was applied for two hours, using the column bypass, with a gentle nitrogen flow. The reaction mixture was cooled to 130° C. and diluted with 177.5 g n-butyl acetate. The product was cooled to 50-60° C. and filtered over 10 microns filter cloth. A thiol-functional polyester was obtained. The thiol-functional polyester did not contain residual methane sulfonic acid catalyst (<20 ppm detection limit). GPC showed an Mn of 1,122 and an Mw of 2,663. The polyester had a C/HA of 2.59 and a theoretical SH-functionality of 3.0.

A small amount of resin was evaporated to dryness and a viscosity of 211 Pa·s was measured for this dried sample, using cone #6 @ 20 rpm.

Example 7

Preparation of a Thiol-Functional Compound

In a 2-liter four-necked round-bottomed flask equipped with mechanical stirrer, thermocouple, Vigreux column, distillation equipment and nitrogen inlet the following materials were charged: pentaerythritol (175.26 gram), Pripol 1009 (370.98 gram), 3-mercapto propionic acid (273.56 gram), triphenyl phosphite (1.63 gram) and xylene (160 gram). The batch was made inert by breaking a vacuum with a nitrogen flow. This was repeated 3 times. Batch temperature was set to 150° C. If necessary more xylene was added to maintain a gentle reflux. The reaction water was distilled off. When 67% of the theoretical amount of water had been distilled off, 0.8 grams of methane sulfonic acid were added. When necessary another 0.8 grams of methane sulfonic acid were added.

The reaction was continued until an acid value of less than 3 mg KOH/gram was obtained. The xylene was then distilled off using a vacuum. The residue was a liquid having a viscosity of 40 Pa·s at 23° C.

Assuming that Pripol 1009 is the dimer of the $C_{18}$ fatty acid, the material has a theoretical thiol functionality of 4, a theoretical molecular formula $C_{58}H_{104}O_{14}S_4$ and a C/HA of 3.22.

The invention claimed is:

1. A thiol-functional organic compound comprising on average at least 3.1 thiol groups per molecule, and comprising carbon atoms, oxygen atoms, and sulfur atoms, and optionally further heteroatoms, and wherein the ratio of the number of carbon atoms (C) to the sum of the number of heteroatoms (HA), (C/HA) is at least 2.0, and wherein the thiol functionality is provided by a group selected from 2-mercapto acetyl, 2-mercapto propionyl, 3-mercapto propionyl, and combinations thereof, and wherein the compound further additionally comprises one or more hydroxyl groups, and wherein the thiol-functional compound is obtained by reaction of a part of the thiol groups of a thiol-functional precursor compound with an epoxide-functional or acryloyl-functional compound.

2. The thiol-functional compound according to claim 1, wherein the compound is liquid at 23° C.

3. The thiol-functional compound according to claim 2, wherein the compound has a viscosity at 23° C. in the range of 2 to 100 Pas.

4. The thiol-functional compound according to claim 1, wherein the compound has on average at most 7 thiol groups per molecule.

5. The thiol-functional compound according to claim 1, wherein the thiol-functional compound has a surface tension of at most 45 dyne/cm.

6. A liquid coating composition comprising the thiol-functional compound according to claim 1 and a thiol-reactive crosslinker.

7. The coating composition according to claim 6, wherein the thiol-reactive crosslinker is a polyisocyanate.

8. The coating composition according to claim 6, wherein the coating composition is a non-aqueous coating composition.

9. The coating composition according to claim 1, wherein the coating composition is a non-aqueous coating composition.

10. The thiol-functional compound according to claim 2, wherein the compound has on average at most 7 thiol groups per molecule.

11. The thiol-functional compound according to claim 3, wherein the compound has on average at most 7 thiol groups per molecule.

12. The thiol-functional compound according to claim 4, wherein the thiol-functional compound has a surface tension of at most 45 dyne/cm.

13. The thiol-functional compound according to claim 1, wherein the thiol-functional compound has a surface tension of at most 45 dyne/cm.

* * * * *